(12) United States Patent
van Dijk (10) Patent No.: US 11,019,806 B2
(45) Date of Patent: Jun. 1, 2021

(54) METHOD AND SYSTEM FOR DETERMINING A PHYSIOLOGICAL CONDITION OF A RUMINANT

(71) Applicant: N.V. Nederlandsche Apparatenfabriek NEDAP, Groenlo (NL)

(72) Inventor: Jeroen Martin van Dijk, Groenlo (NL)

(73) Assignee: N.V. NEDERLANDSCHE APPARATENFABRIEK NEDAP, Groenlo (NL)

( * ) Notice: Subject to any disclaimer, the term of this patent is extended or adjusted under 35 U.S.C. 154(b) by 230 days.

(21) Appl. No.: 15/287,289

(22) Filed: Oct. 6, 2016

(65) Prior Publication Data

US 2017/0112104 A1 Apr. 27, 2017

(30) Foreign Application Priority Data

Oct. 6, 2015 (NL) ...................................... 2015574

(51) Int. Cl.

| A01K 29/00 | (2006.01) |
| A61B 5/00 | (2006.01) |
| A61B 5/11 | (2006.01) |
| A01K 27/00 | (2006.01) |
| G06N 3/04 | (2006.01) |
| G06N 3/08 | (2006.01) |

(52) U.S. Cl.
CPC .......... A01K 29/005 (2013.01); A01K 27/009 (2013.01); A61B 5/1118 (2013.01); A61B 5/42 (2013.01); A61B 5/4809 (2013.01); A61B 5/7264 (2013.01); G06N 3/0472 (2013.01); G06N 3/08 (2013.01); A61B 5/6822 (2013.01); A61B 5/6829 (2013.01); A61B 5/7267 (2013.01); A61B 2503/40 (2013.01); A61B 2562/0219 (2013.01)

(58) Field of Classification Search
None
See application file for complete search history.

(56) References Cited

U.S. PATENT DOCUMENTS

| 2009/0187392 A1 | 7/2009 | Riskey et al. |
| 2015/0070172 A1 | 3/2015 | Alasaarela |
| 2015/0185088 A1 | 7/2015 | Rabieirad et al. |

(Continued)

FOREIGN PATENT DOCUMENTS

| WO | 2005/115242 A2 | 12/2005 |
| WO | 2011/069512 A1 | 6/2011 |

OTHER PUBLICATIONS

"Public Views on Artificial Intelligence and Intellectual Property Policy" Oct. 2020 USPTO https://www.uspto.gov/sites/default/files/documents/USPTO_AI-Report_2020-10-07.pdf.*

(Continued)

*Primary Examiner* — Bradley Smith
(74) *Attorney, Agent, or Firm* — Jacobson Holman PLLC (57) ABSTRACT

The invention provides a system and a method for determining a physiological condition of a ruminant. The system comprises a sensor unit and a calculating unit. The sensor unit generates a stream of measuring data that are indicative of a movement condition of the ruminant. The calculating unit uses a neural network for calculating a stream of condition data from the stream of measuring data. The condition data indicate a physiological condition of the ruminant.

16 Claims, 4 Drawing Sheets

(56) References Cited

U.S. PATENT DOCUMENTS

2015/0359199 A1* 12/2015 Schaefer .............. A01K 29/005
362/110

OTHER PUBLICATIONS

P. Martiskainen et al., "Cow behaviour pattern recognition using a three-dimensional accelerometer and support vector machines", Applied Animal Behaviour Science, vol. 119, Apr. 5, 2009, pp. 32-38 (7 pages).
Dutch Search Report, dated Jul. 27, 2016 (3 pages).

* cited by examiner

METHOD AND SYSTEM FOR DETERMINING A PHYSIOLOGICAL CONDITION OF A RUMINANT

BACKGROUND OF THE INVENTION

Ruminants have four stomachs: the rumen, the reticulum, the omasum and the abomasum. A ruminant first chews the food superficially, after which it ends up in the reticulum and the rumen. After about half an hour the coarse-fibrous materials return as chymes to the mouth where they are masticated and admixed with saliva. Upon return in the rumen, the fine materials proceed via the reticulum to the omasum for the further digestion.

The share of time of the different physiological activities of the ruminant is an important indicator of its state of health. This can be taken into account in the composition of the dietary pattern or the schedule of the daily rhythm, such as the switching times for barn lighting and the times at which the ruminants are milked. With ruminants, ruminating is an important physiological activity besides eating, resting, and sleeping. The ruminant can take both a standing and a lying posture in ruminating.

CROSS-REFERENCE TO RELATED APPLICATIONS

"Not Applicable"

STATEMENT REGARDING FEDERALLY SPONSORED RESEARCH OR DEVELOPMENT

"Not Applicable"

THE NAMES OF THE PARTIES TO A JOINT RESEARCH AGREEMENT

"Not Applicable"

STATEMENT REGARDING PRIOR DISCLOSURES BY THE INVENTOR OR A JOINT INVENTOR

"Not Applicable"

BRIEF SUMMARY OF THE INVENTION

It is an object of the invention to enable the activities mentioned to be established in a simple manner.

To realize this object, the invention provides a system as described in claim 1.

For realization of this same object, the invention further provides a method as described in claim 13.

The present invention is based on the insight that the activities mentioned can be reliably established from movement condition data of the ruminant with the aid of a neural network.

Establishing the movement condition data can be done without this entailing any appreciable hindrance to the ruminant. By processing this data with a neural network, the activities mentioned can then be easily established.

A neural network can be trained for this purpose by making use of a series of input data, with respective input data giving an indication of the physiological condition of the ruminant for the respective time intervals based on an independent assessment, for instance an assessment obtained from an expert who either observes the ruminants directly or from camera pictures. During training, the neural network adapts its settings until the physiological condition that has been established by the neural network on the basis of movement condition data for different time intervals substantially corresponds to the physiological condition that has been established for those time intervals on the basis of the independent assessment.

The thus trained neural network can then be used to establish the activities on the basis of movement condition data. Alternatively, or additionally, the settings of the trained neural network may be copied to other neural networks, which are then applied for establishing the activities.

A neural network is a calculating unit which comprises a plurality of mutually linked network cells, where the network cells can generate an output signal that is based on a plurality of mutually weighed input signals, while the weighing factors used for weighing the input signals can be adapted by training the network. The neural network is supplied with both input signals and control signals enabling the neural network to establish in what measure the condition data calculated on the basis of the weighing factors correspond to the actual condition. The control signals may indicate the actual condition directly, or may be indicative of a deviation of the calculated condition data and the condition data representing the actual condition.

Examples of a neural network are the (multilayer) perceptron, the Kohonen network, the Hopfield network, the Boltzmann machine, the radial basis function network, the support vector machine, and the self-organizing map.

The above neural networks can be developed in hardware, with each component in the neural network, comprising the network cells, the connections and weighing elements for weighing the different signals, being provided as a respective component in the hardware. On the other hand, a neural network may also be simulated by software that is executed on a programmable processor, whereby the processor executes the operations to be executed by the different components of the network. Also intermediate solutions are possible. The programmable processor can have, for example, different 'cores' each executing a part of the operations for a respective section of the network. In a programmable processor with four cores, for example, each core can simulate a respective layer of the neural network.

For training a neural network it is desired that the weighing factors used are adjustable, in order to provide that the neural network with the settings obtained during the training can make a reliable estimate of the condition of the ruminant on the basis of the movement condition data. If desired, but not necessarily so, the weighing factors may be fixed in the neural network intended for end use. In a hardware implementation of the neural network intended for end use, the weighing factors may be fixed in the design thereof. In an implementation of the neural network intended for end use in software to be executed by a programmable processor, the software with the weighing factors may be additionally supplied, for example as a ROM.

In an embodiment, the neural network has respective outputs for delivering a signal that is indicative of a probability that the physiological condition of the ruminant corresponds to respective specific physiological conditions. The physiological conditions for which the neural network has a respective output include, for example, at least one or more of pasture, pasturing, grazing, eating, ruminating, resting, sleeping, standing and lying.

In an embodiment, the neural network has a respective output for at least one or more of the physiological conditions designated as resting, ruminating and eating. The neural network can furthermore have an output for delivering a signal that indicates the probability that the physiological condition of the ruminant is a different one than these physiological conditions.

In an embodiment, the neural network has a respective output for at least one or more of the physiological conditions designated as resting and eating. The neural network may furthermore have an output for delivering a signal that indicates the probability that the physiological condition of the ruminant is a different physiological condition, not being ruminating, than these physiological conditions.

In an embodiment, the neural network has a respective output for at least one or more of the physiological conditions designated as resting, and sleeping.

In an embodiment, the neural network has a respective output for at least one or more of the physiological conditions designated as standing, and lying.

Preferably, the system comprises a system part to be worn by the ruminant, that is included in a housing to be worn by the ruminant around the neck. It has appeared that from the movements of the neck of the ruminant a lot of information can be derived about the physiological condition of the ruminant. It has appeared that especially a 3G sensor is highly suitable for this.

BRIEF DESCRIPTION OF THE SEVERAL VIEWS OF THE DRAWING(S)

These and other aspects of the current invention are further elucidated on the basis of the following drawings, in which.

DETAILED DESCRIPTION OF THE INVENTION

In the following figures corresponding parts have the same reference numerals.

Figure 1:
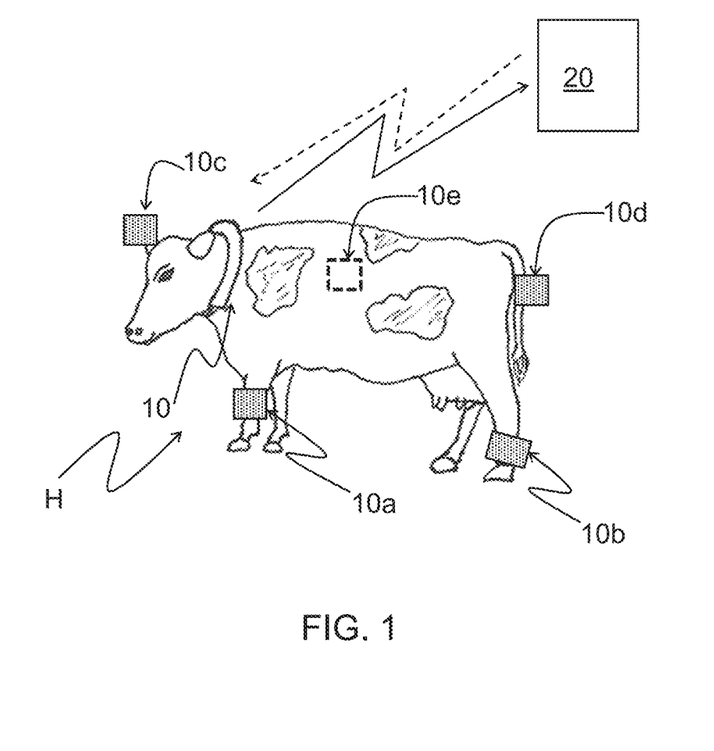
FIG. 1 schematically shows a system for determining a physiological condition of a ruminant, FIG. 2 schematically shows a system part, to be worn by the ruminant, of the system of FIG. 1.

FIG. 1 schematically shows a system 10, 20 for determining the condition of a ruminant H. In the embodiment shown, the system is implemented as a first system part 10 which is arranged as a collar around the neck of the ruminant and a second system part 20 which is disposed elsewhere and which receives signals from the first system part 10 in a wireless manner, for example, directly via a wireless connection or through intervention of a network, for example an internet connection. As is elucidated further on in the description, however, many other implementations are possible.

Figure 2:
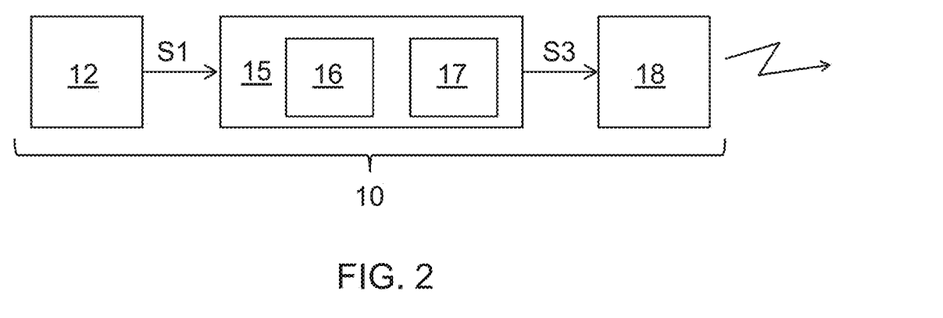

The system part 10, which is shown in more detail in FIG. 2, comprises a sensor unit 12 for generating a stream 81 of measuring data which are indicative of a movement condition of the ruminant. In operation, the sensor unit 12 generates a stream of measuring data S1 which is indicative of a movement condition of the ruminant H. For that purpose, the sensor unit 12 is equipped, for example, with one or more inertia sensors, and/or gyroscopes. The system part furthermore comprises a calculating unit 15. The calculating unit 15 utilizes a neural network for calculating a stream S3 of condition data from the stream of measuring data.

As a neural network, a feedforward network can be applied, but also a recurrent network may be applied, which is for example configured as a feedforward network. Examples are the perceptron, the Kohonen network, the Hopfield network, the Boltzmann machine, the radial base function network, the support vector machine and the self-organizing map.

The condition data S3 are indicative of the physiological condition of the ruminant. The condition data can indicate, for example, whether the ruminant at a particular moment, or during a particular time interval, is engaged in eating, in ruminating the food, or that the ruminant is resting, or sleeping. Also, the condition data can indicate whether the ruminant is doing so standing up or lying down. On the basis of obtained condition data, it can thereupon be established, in turn, what share of time the ruminant spends in which condition, for instance, it may be established how many hours a day the ruminant sleeps, rests, eats, ruminates, etc. Also, the current condition of the animal may be determined continuously, for an indefinite period.

In the exemplary embodiment shown in FIG. 2 the system part worn by the ruminant furthermore has a transmitting unit 18. This transmitting unit 18 forwards the obtained condition information to a second system part 20 which is equipped with a receiving unit for receiving the forwarded condition information. In an embodiment (as schematically indicated by the broken-line arrow), also means are provided that enable the second system part 20 to send signals to the first system part 10, for instance to confirm receipt of the condition information, or to influence the operation of the first system part 10, for instance to indicate at what intervals the first system part 10 is to forward the condition information to the second system part 20.

Figure 3:
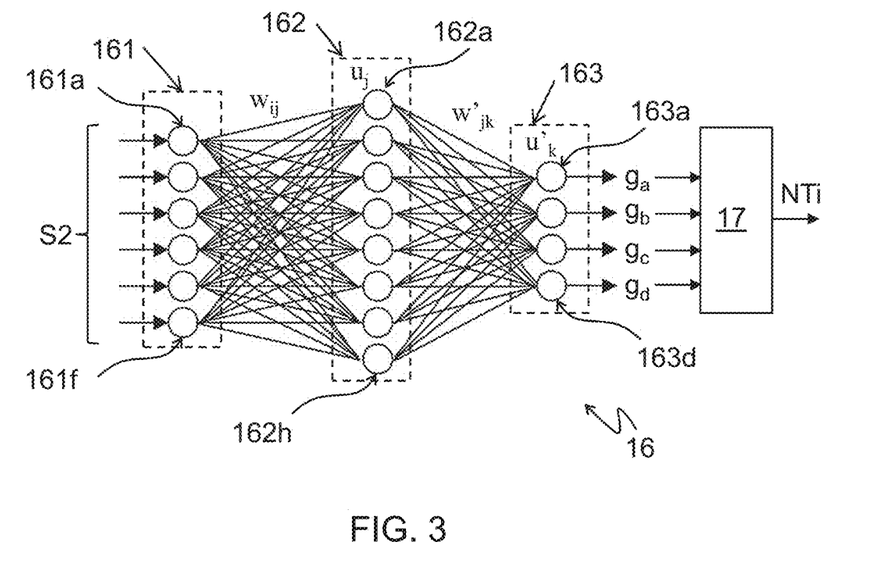
FIG. 3 shows an example of a neural network used in the system part of FIG. 2.

FIG. 3 shows in more detail an embodiment of a neural network 16 which can be used by the calculating unit 15 to calculate condition data from the stream of measuring data. In the embodiment shown, the neural network has three layers 161, 162, 163, but in other embodiments more or fewer layers may be provided. The first layer 161 receives input data S2 which are indicative of a movement condition of the ruminant, for instance the measuring data ax(n), ay(n), az(n). In this implementation the first layer 161 has six network cells 161a, . . . , 161f. Each of these six network cells periodically receives an input datum that is specific for an aspect of movements of the ruminant, for example information about the magnitude of the acceleration in a specific direction in the coordinate system of the sensor unit 12, or information from a gyroscope included in the sensor unit. The first layer 161 of network cells 161a, . . . , 161f, can for instance temporarily store the received data and then pass it on unmodified to the second layer 162, but alternatively may perform a weighing or other operation, for instance limiting the signal within a minimum and a maximum value.

The second, hidden, layer 162 comprises network cells 162a, . . . , 162h. Each of these network cells 162j (j=a, . . . , h) calculates an output value $v_j$, on the basis of a function f of the data $v_a, \ldots, v_f$ passed on, whether or not processed or weighed, by the first layer 161.

$$f_j(v_a, \ldots, v_f)$$

In the exemplary embodiment shown, the function applied is defined as follows:

$$f_j(v_a, \ldots v_f) = \sum_{i=a,.}^{f} w_{ji} v_i$$

Other functions, however, are also possible.

The third layer 163 with network cells 163a, ..., 163d, calculates an output value $v_k$, on the basis of a function g of the output values calculated by the second layer 162 on the basis of the functions $f_j$, for example as follows:

$$g_k(f_a, \ldots f_h) = \sum_{j=a,.}^{h} w'_{kj} f_j$$

Each function value $g_k$ is an indication of the probability that the ruminant is in a specific condition. In an exemplary embodiment, the function values $g_a, \ldots, g_d$ furnished by the network cells 163a, ..., 163d are, respectively, indications of the probability that the ruminant is resting, ruminating, eating, or engaged in another activity. In other embodiments, network cells may be provided for delivering a probability indication of yet other possible conditions of the ruminant, for example, an indication of the probability that the ruminant is standing or lying. Combinations are also possible, for example, network cells that deliver an indication of the probability that the ruminant is resting, ruminating, eating, and further network cells that are indicative of the probability that the ruminant, while doing so, is standing or lying.

Also, the neural network may be provided with outputs for delivering a signal that is indicative of a probability that the physiological condition of the ruminant does not correspond to one or more physiological conditions. A network 163 may, for example, for each of the physiological conditions of resting, ruminating and eating have a primary output for a signal that indicates the probability of each of those conditions, and in addition the network can have a secondary output for a signal that indicates the probability that the physiological condition of the ruminant is a different one than these physiological conditions of resting, ruminating and eating.

Also, the signal at such a secondary output may be co-indicative of the probability that a different condition than the conditions for which primary outputs are provided, is absent. For example, the neural network can have a primary output to indicate the probability that the ruminant is resting; have another primary output to indicate the probability that the ruminant is eating and in addition have a secondary output for delivering a signal indicating the probability that the ruminant is not resting, not eating and not ruminating either.

It is noted, perhaps unnecessarily, that the neural network can have more of such first-mentioned or secondly-mentioned secondary outputs.

In the embodiment shown, the neural network 16 calculates a probability indication for each of the above-mentioned conditions. The duration of the time intervals between successive calculations may for instance be in the range of 10 s to 10 min. According as the time interval is longer, and hence the sensor unit 12 and the calculating unit 15 need to be active less often, the first system part 10 can remain operational longer with a given battery capacity, and/or a smaller battery will suffice. With a very long time interval, for example longer than one hour, the obtained condition information is too limited to get a good impression of the physiological condition of the ruminant. With a very short time interval, for example shorter than one second, the additionally obtained condition information has only a limited added value and this might not outweigh the relatively high energy consumption. With a very small time interval there is in effect a continuous determination of the current condition of the animal for an indefinite period. In a practical embodiment the time interval can be, for example, about one minute.

On the basis of the probability indications supplied by the network cells 163a, ..., 163d it can be established with a further calculating module 17 which is the most probable condition Ti that the ruminant is in. For example, the condition designated as the most probable condition Ti is the condition that has the highest probability indication g.

$$T_i = \underset{i=a,\ldots,d}{\arg\max} \, g_i$$

But other factors may be taken into account as well. For example, it may be concluded that it's unlikely that the ruminant is ruminating if earlier-supplied probability indications indicate that the ruminant has not eaten for a prolonged period of time.

In the embodiment shown, it is established per time interval $t_1$-$t_2$ how often each of the possible conditions has been indicated as the most probable condition.

$$NT_i = \sum_{t=t_1}^{t_2} T_i(t)$$

Possibly, from the thus obtained counting values $NT_i$ it may in turn be established for each possible condition which condition TTi has the highest counting value and, if desired, it can be designated as the most probable condition TTi for the entire time interval $t_1$-$t_2$.

The time interval $t_1$-$t_2$ can be, for example, one minute. Then, for example, it may furthermore be counted with the aid of the calculating module 17 for each quarter of an hour how long an animal has been in a particular condition. This information may for instance be buffered in the calculating module for 96 quarters of an hour after which the contents of the buffer are transmitted with the transmitting unit 18.

Another possibility would be that for each of the possible conditions the calculated probability indications are added up and, as most probable condition TTi for the entire time interval $t_1$-$t_2$, the condition is designated that has the highest cumulative probability indication.

In an embodiment, the counting value NTi for each condition i is calculated for a time interval having a duration of about 5 to 25 times the duration of the time intervals between successive calculations of the probability indications gi. In a practical embodiment in which a most probable condition Ti is established every minute, the duration of the time intervals $t_1$-$t_2$ is, for example, about a quarter of an hour.

The counting values NTi can be sent to the second system part 20 directly, but it's more favorable to send the data batchwise. Since transmission thus entails less overhead, on average, less energy will suffice. In a practical embodiment, for example, the transmitting unit 18 periodically transmits a batch of a few tens up to a few hundreds of sets of counting values NTi. For example, daily a buffer of 96 sets of counting values NTi (i=a, . . . , d) is sent to the second system part 20 for further analysis. The point of time at which the indications NTi are sent may for instance be chosen such that there's an opportunity to make adjustments in the circumstances of the ruminant directly, for example adjustments in the diet, the lighting or to the schedule of the day.

Many variations on the above-described embodiments are possible. In other embodiments, signal transfer from the first to the second system part can proceed, for example, via a (detachable) lead, or via a detachable data carrier, such as a flash memory. Also, embodiments are conceivable in which the calculating unit 15 is accommodated in the second system part 20 instead of in the first system part 10. In that case, the transmitting unit 18 sends the measuring data needed for the calculating unit 15 to the second system part 20. This, too, could be done batchwise. In practice, however, it is more favorable that the calculating unit 15 is part of the first system part 10 worn by the ruminant.

The system part 10 may also be worn by the ruminant in a different manner, for example as a strap 10a, 10b around one of the legs, as a tag 10c to the ear, as a sticker 10d on the skin, or as an implant 10e. In yet other embodiments, the system may be of one-part design, and, for example, provide the possibility of reading out data on a screen.

Summarizing, the above-described system in operation carries out a method having the following steps.

With movement sensors, for example, accelerometers, gyroscopes, and the like, a stream S1 of measuring data, e.g. ax(n), ay(n), az(n), is generated that is indicative of a movement condition of the ruminant. Then, with a neural network a stream S3 of condition data T(m) is calculated from the stream of measuring data. These condition data are indicative of the physiological condition of the ruminant. Generating the measuring data and calculating the condition data therefrom can take place at the same time, in the sense that new measuring data can be generated while condition data are being determined from earlier-generated measuring data.

The neural network 16 that is used may have been prepared for this purpose in advance, for example by adopting settings (e.g. the weighing factors $w_{ij}$, $w'_{jk}$) from an earlier-trained neural network. On the other hand, the neural network 16 itself may be trained with a training prior to the use, for example as described in the following procedure.

Just as in the above-described method, a stream S1 of measuring data, e.g. ax(n), ay(n), az(n), is generated that is indicative of a movement condition of the ruminant for which the network will also be used later to determine condition data of the ruminant as described above.

In addition, a series of input data associated with the measuring data is received about the physiological condition of this ruminant, which input data have been obtained on the basis of an independent assessment. This input data has for instance been obtained with the aid of an expert who observes the ruminant and each time indicates for different parts of the measuring data what in his/her opinion the condition of the ruminant is. Observation can for instance take place directly, but alternatively by means of video pictures.

With the aid of the measuring data and the associated input data obtained independently thereof, the neural network can be trained. This is to say that the settings, such as the weighing factors, of the neural network are adjusted until the condition Ti that has been established by the network 16 substantially corresponds to the data that have been obtained by independent assessment. If desired, after training, the functioning of the neural network 16 can be verified with control data, i.e., a part of the independently obtained data may be excluded from use for the training and be reserved to establish whether the condition Ti predicted by the trained network corresponds to the condition of the ruminant that applies according to these control data.

Figure 4:
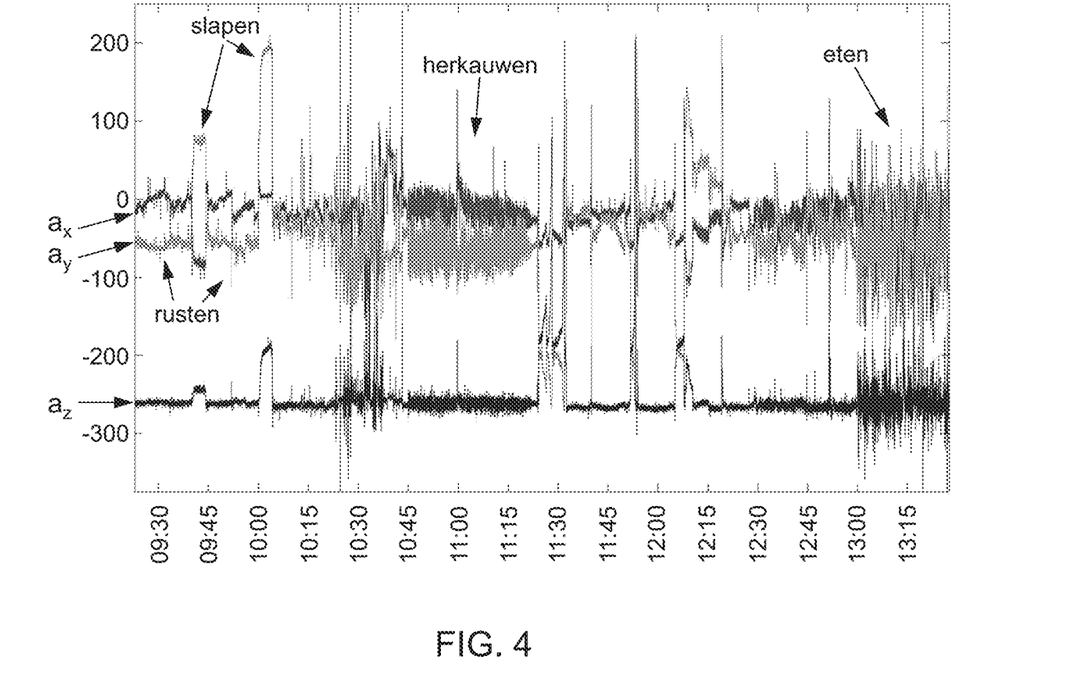
FIG. 4 shows measuring values and other data that were used for training the neural network.

All this is illustrated in FIG. 4. FIG. 4 shows the measured values of the acceleration $a_x$, $a_y$, $a_z$ in the direction of three mutually orthogonal axes x,y,z. For several time intervals a series of input data has been received about the physiological condition of the ruminant, which input data have been obtained on the basis of an independent assessment. These data are schematically shown in FIG. 4 as "resting", "sleeping", "ruminating" and "eating", but are supplied to the neural network as digital information, for instance, these are indicated with the numerals 1 through 4.

In this manner, for each of a plurality of time intervals a most probable condition Ti can be predicted, and it can be compared with the assessment of the condition of the ruminant on the basis of the independently obtained data. The deviation between these two values is used for adjustment of the settings of the neural network. Suitable algorithms for this are known per se. These are usually based on a "gradient descent" method. For perceptrons this type of method is for instance known as "back propagation". The order in which the signals of a particular time interval are supplied to the neural network is not relevant. What is important is that it holds for each time interval that it comprises a stream of measuring data that is associated with a single movement condition of the ruminant. For the training of the network in order for it to be able to recognize mutually different movement conditions, there are needed, in particular, different streams of measuring data that are associated with different movement conditions of the ruminant.

An overview of suitable neural networks and methods of training them is available in:
http://www.cs.put.poznan.pl/jstefanowski/sed/DM13neuralnetworks.pdf In the preceding example, the network was trained on the basis of measuring data and input data obtained from the same ruminant as for which the network, after training, will be used for determining the condition of this ruminant. It holds for this, for instance, that the method for training comprises the following steps:

a. generating at least one stream (S1) of measuring data that is indicative of a movement condition of the first ruminant, b. receiving input data that are associated with the at least one stream of measuring data of step a., these input data giving an indication of the physiological condition of the first ruminant for said at least one stream of measuring data on the basis of an independent assessment, c. training a neural network on the basis of the stream (S1) of measuring data generated in step a. and the associated input data received in step b.

In particular, the method furthermore comprises the following steps:

d. repeating steps a., b. and c. for another stream of measuring data and associated other input data, each relating to the first ruminant. It is also possible, however, that the network is trained on the basis of measuring data and input data of another ruminant, all this in a same manner as described above. It holds for this, for instance, that the method for training furthermore comprises the following steps:

a1. generating at least one stream (S1) of measuring data that is indicative of a movement condition of a second ruminant which is different than the first ruminant, b1. receiving input data that are associated with the at least one stream of measuring data of step a1., these input data giving an indication of the physiological condition of the second ruminant for said associated at least one stream of measuring data of step a1. on the basis of an independent assessment, c1. training a neural network on the basis of the stream (S1) of measuring data generated in step a1. and the associated input data received in step b1.

In particular, this method furthermore comprises the following steps:

d1. repeating steps a1., b1. and c1. for another stream of measuring data and associated other input data, each relating to the second ruminant. Also, the network may be trained on the basis of measuring data and input data of a group of ruminants which may or may not comprise the ruminant for which the trained network will be used later to determine the condition. In such a case, on the one hand the measuring data belonging to a particular condition can be averaged over the group and on the other hand the input data associated with the measuring data and belonging to the particular condition can be determined. This is then repeatedly carried out for the different conditions and on the basis of this information the network is trained. It holds for this, for instance, that the method furthermore comprises prior to the normal use of the neural network:

a2. generating a plurality of streams (S1) of measuring data that are indicative of a same movement condition of, respectively, each of a plurality of ruminants, b2. receiving input data that are associated with the plurality of streams of measuring data of step a2., these input data giving an indication of the same physiological condition mentioned in step a2. on the basis of an independent assessment, c2. training a neural network on the basis of the streams (S1) of measuring data generated in step a2. and the associated input data received in step b2.

In particular, this method furthermore comprises the following steps:

d2. repeating steps a2., b2. and c2. for another plurality of measuring data and associated other input data, each relating to the plurality of ruminants.

Figure 5:
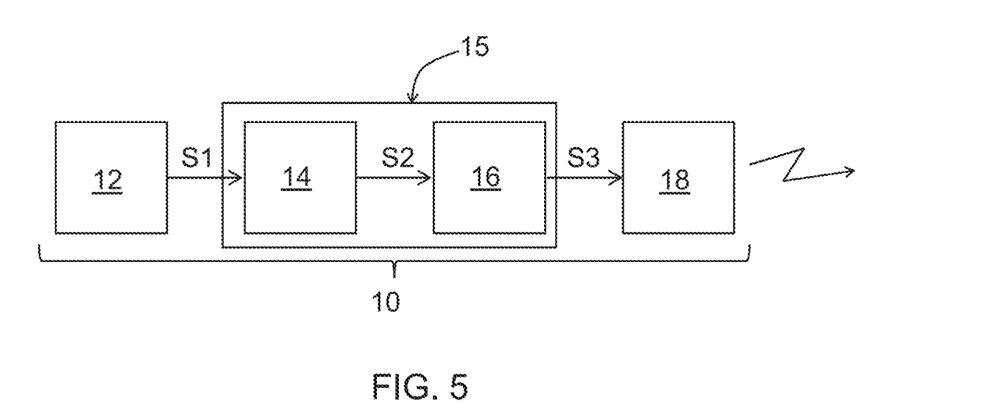
FIG. 5 shows an alternative embodiment of a system part to be worn by the ruminant.

In an embodiment, during training and use of the trained neural network, or a copy thereof, a pre-processing operation can take place of the stream S1 of measuring data before these are used for establishing a most probable condition Ti. This further embodiment is schematically shown in FIG. 5. The calculating unit 15 then has an additional calculating module 14. In operation, the additional calculating module 14 derives from the stream of measuring data S1 a stream S2 of derived data, whereby individual data in the stream of derived data have been calculated from a plurality of measuring data in the stream S1 of measuring data. On the one hand, it is for instance possible, for each point of time for which measuring data are available, to calculate a derived datum from a series of measuring data which have been obtained at points of time in a period of time around, or following, that point of time. Preferably, however, the derived data are calculated for a part of the points of time for which measuring data are available. For instance, for mutually successive periods of time, in each case a derived datum is (or derived data are) calculated only for a single point of time in the respective period of time. Doing so, a data reduction can be accomplished which simplifies a further processing by the neural network 16.

In an embodiment the sensor unit 12 supplies, for example, a stream of two measuring data per second, and every minute the additional calculating module 14 calculates therefrom one or more derived data that are an indication of a respective property of a signal represented by the measuring data.

For clarity, FIG. 5 does not show a module 17 as in FIG. 2. If so desired, here too, a module 17 may have been added for calculating a counting value NTi per time interval from data about the most probable condition Ti for points of time in that time interval.

Figure 6:
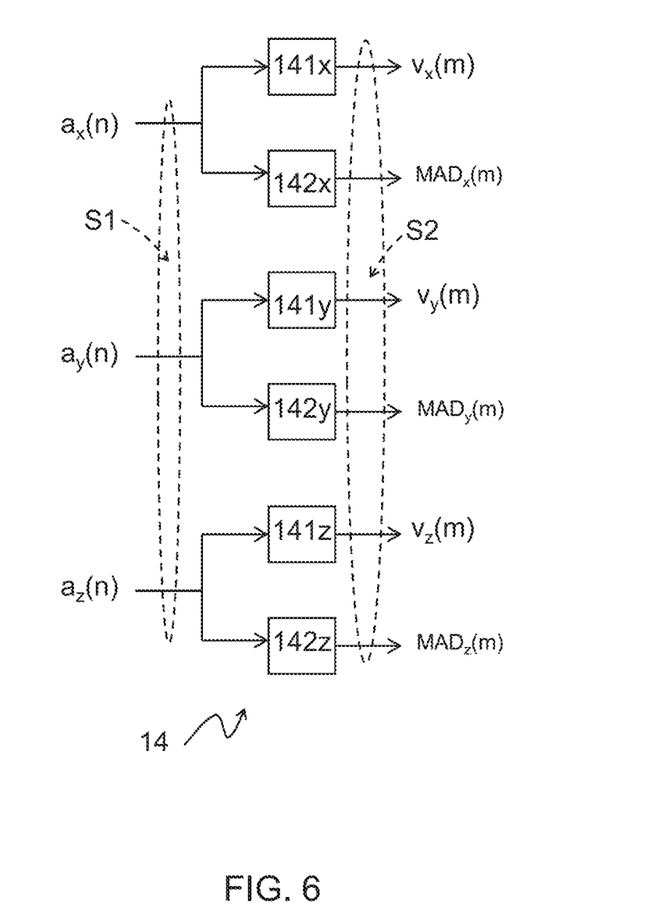
FIG. 6 shows a component of the system part of FIG. 5 in more detail.

FIG. 6 shows an embodiment in which the additional calculating module 14 has a first calculating block 141x, 141y, 141z and a second calculating block 142x, 142y, 142z for calculating an indication of a respective property of a signal represented by the stream of measuring data S1. In the embodiment shown, the sensor unit 12 (FIG. 5) periodically supplies acceleration data $a_x$, $a_y$, $a_z$. This data reflect for successive points of time the acceleration in the coordinate system of the sensor as measured by the sensor unit 12. In the embodiment shown, the first calculating block calculates a variance V in the stream of measuring data as the indication for a first property of the signal represented by the measuring data. Here, $V_x(m)$ is calculated from a series of acceleration values $a_x(n)$ with $n=n_m$ to $n=n_{m+1}$ as:

$$V_x(m) = \frac{1}{N} \sum_{n=n_m}^{n_{m+1}} (a_x(n) - \mu_x)$$

wherein $\mu_x$ is the average value for this series of acceleration values $a_x(n)$, and N ($1+n_{m+1}-n_m$) the number of the values in the series. The number of values in the series can be, for example, between 10 and 1000.

Similarly, the values $V_y(m)$ are obtained from a series of acceleration values $a_y(n)$ and the values $V_z(m)$ are obtained from a series of acceleration values $a_z(n)$.

The second calculating block 142x, 142y, 142z calculates another property of a signal represented by the stream of measuring data S1. Here, this is the average $MAD_x(m)$ of absolute differences between successive measuring data in the stream of measuring data. This can be calculated as follows:

$$MAD_x(m) = \frac{1}{N} \sum_{n=n_m}^{n_{m+1}-1} |a_x(n+1) - a_x(n)|$$

Similarly, the values $MAD_y(m)$ can be obtained from a series of acceleration values $a_y(n)$ and the values $MAD_z(m)$ can be obtained from a series of acceleration values $a_z(n)$.

Also, the first calculating block or second calculating block can determine the average $MEAN_x(m)$ of successive measuring data in the stream. This can be calculated as follows:

$$MEAN_x(m) = \frac{1}{N} \sum_{n=n_m}^{n_{m+1}} a_x(n)$$

Similarly, the values $MEAN_y(m)$ can be obtained from a series of acceleration values $a_y(n)$ and the values $MEAN_z(m)$ can be obtained from a series of acceleration values $a_z(n)$.

Also, the first calculating block or second calculating block can determine the minimum $MIN_x$, $MIN_y$, and $MIN_z$ of successive measuring data in the stream. This can be calculated as follows:

$$MIN_x(m) = \min_{n=n_m \ldots n_{m=1}} a_x(n);$$

$$MIN_y(m) = \min_{n=n_m \ldots n_{m=1}} a_y(n);$$

$$MIN_z(m) = \min_{n=n_m \ldots n_{m=1}} a_z(n)$$

Also, the first calculating block or second calculating block can determine the maximum $MAX_x$, $MAX_y$, and $MAX_z$ of successive measuring data in the stream. This can be calculated as follows:

$$MAX_x(m) = \max_{n=n_m \ldots n_{m=1}} a_x(n);$$

$$MAX_y(m) = \max_{n=n_m \ldots n_{m=1}} a_y(n);$$

$$MAX_z(m) = \max_{n=n_m \ldots n_{m=1}} a_z(n)$$

The results obtained with the pre-processing operations reflect mutually different signal properties. Thus, the value MAD is indicative of relatively fast variations in the measured value of the acceleration, and the value V is indicative of the total of variations in the measured value of the acceleration, the value MEAN is indicative of the average of the measured acceleration, the value MIN is indicative of a lower limit of the measured acceleration and the value MAX is indicative of an upper limit of the measured acceleration. Another derived datum may be the absolute difference between the greatest and the smallest value of the acceleration in the series of acceleration values. This datum is in particular indicative of the strength of relatively slow variations in the acceleration.

These pre-processing operations convert the stream of measuring data S1 into a stream of derived data S2 with lower frequency. This is not essential, but does simplify the task of the neural network, so that, in particular, it can be trained faster to recognize specific conditions. In a practical embodiment, the sensor unit supplies, for example, two measuring data per second for each measuring direction x, y, z, and every minute the calculation blocks $141x,y,z$ and $142x,y,z$ calculate a derived datum from the measuring data supplied in the past minute.

In this document the indefinite article "a(n)" is used in the sense of "one or more", as is conventional in patent documents. The wording "comprises" is not used exclusively. In other words, if in this document it is stated that a first element comprises a second element, the first element can also comprise other elements besides the second element. Furthermore, in this document the term "or" is used in a non-exclusive sense. That is to say, "A or B" covers "A but not B", "B, but not A" and "A and B", unless indicated otherwise.

The invention claimed is:

1. A system for determining a physiological condition of a ruminant, which system comprises the following components:
 an inertia sensor or a gyroscope for collecting and generating a first stream (S1) of measuring data ($a_x(n)$, $a_y(n)$, $a_z(n)$) that are indicative of a movement condition of the ruminant,
 an additional calculating module for deriving from the first stream of measuring data (S1) a second stream (S2) of derived data with a frequency lower than that of the first stream of measuring data, whereby individual data in the second stream of derived data have been calculated from a plurality of measuring data in the first stream S1 of measuring data,
 a neural network for calculating a third stream (S3) of condition data ($NT_i$) from the second stream of derived data, which condition data are indicative of the physiological condition of the ruminant,
 an output device wherein the neural network has respective outputs through the output device for delivering a signal ($g_i$) that is indicative of a probability that the physiological condition of the ruminant corresponds to respective specific physiological conditions, characterized in that the physiological conditions for which the neural network has a respective output comprise at least resting;
 wherein the sensor unit comprises an inertia sensor or a gyroscope; and
 wherein the neural network comprises one of perceptron, a Kohonen network, a Hopfield network, a Boltzmann machine, a radial base function network, a support vector machine or a self-organizing map.

2. The system according to claim 1, wherein the physiological conditions for which the neural network has a respective output furthermore comprise at least one or more of eating, ruminating, sleeping, standing and lying.

3. The system according to claim 2, wherein the physiological conditions for which the neural network has a respective output comprise at least one or more of resting, ruminating and eating and the neural network furthermore has an output for delivering a signal that is indicative of a probability that the physiological condition of the ruminant is a different one than these physiological conditions.

4. The system according to claim 2, wherein the physiological conditions for which the neural network has a respective output comprise at least one or more of resting, and sleeping.

5. The system according to claim 2, wherein the physiological conditions for which the neural network has a respective output comprise at least one or more of standing and lying.

6. The system according to claim 1, wherein the physiological conditions for which the neural network has a respective output comprise at least one or more of eating, ruminating, resting, sleeping, standing and lying.

7. The system according to claim 1, wherein the system comprises a system part to be worn by the ruminant.

8. The system according to claim 7, wherein the system part to be worn by the ruminant is included in a housing to be worn by the ruminant around the neck.

9. The system according to claim 7, comprising a transmitting unit and a receiving unit, wherein the inertia sensor or the gyroscope, the neural network and the transmitting unit are part of a first system part to be worn by the ruminant, and wherein the receiving unit is separately included in a second system part, wherein the transmitting unit brings about that the condition data ($NT_i$) calculated by the neural network are transferred to the receiving unit of the second system part, possibly in combination with an identification code.

10. The system according to claim 9, wherein the first system part furthermore comprises a storage unit for storing a plurality of condition data and the transmitting unit brings about that the plurality of condition data are jointly transferred as a cluster of data to the receiving module of the second system part.

11. The system according to claim 1, wherein the inertia sensor or the gyroscope comprises a 3G sensor.

12. The system according to claim 1, wherein the first stream of measuring data (S1) comprises acceleration data.

13. The system according to claim 1, wherein the additional calculating module has a first calculating block and a second calculating block for calculating an indication of a respective property of a signal represented by the first stream of measuring data (S1), wherein the first calculating block calculates a variance V in the first stream of measuring data as the indication for a first property of the signal represented by the measuring data, and wherein the second calculating block calculates a property other than the variance.

14. The system according to claim 13, wherein the property calculated by the second calculating block is selected from the group consisting of a maximum absolute difference between successive measuring data in the first stream of measuring data, the average of successive measuring data in the first stream of measuring data, a minimum of successive measuring data in the first stream of measuring data, a maximum of successive measuring data in the first stream of measuring data.

15. A system for determining a physiological condition of a ruminant, which system comprises the following components:
- an inertia sensor or a gyroscope for collecting and generating a first stream (S1) of measuring data ($a_x(n)$, $a_y(n)$, $a_z(n)$) that are indicative of a movement condition of the ruminant,
- an additional calculating module for deriving from the first stream of measuring data (S1) a second stream (S2) of derived data with a frequency lower than that of the first stream of measuring data, whereby individual data in the second stream of derived data have been calculated from a plurality of measuring data in the first stream S1 of measuring data,
- a neural network for calculating a third stream (S3) of condition data ($NT_i$) from the second stream of derived data, which condition data are indicative of the physiological condition of the ruminant, wherein the neural network is a calculating unit which comprises a plurality of mutually linked network cells, where the network cells can generate the second stream (S3) of the condition data ($NT_i$) from a plurality of mutually weighed input signal of the first stream of the measuring data, while the weighing factors used for weighing the input signals are adapted by training the network, and wherein the weighing factors of the neural network are adjusted until the condition Ti that has been established by the neural network corresponds to data that have been obtained by independent assessment,
- an output device wherein the neural network has respective outputs through the output device for delivering a signal ($g_i$) that is indicative of a probability that the physiological condition of the ruminant corresponds to respective specific physiological conditions, characterized in that the physiological conditions for which the neural network has a respective output comprise at least resting;
- wherein the sensor unit comprises an inertia sensor or a gyroscope; and
- wherein the neural network is selected from one of: perceptron, a Kohonen network, a Hopfield network, a Boltzmann machine, a radial base function network, a support vector machine and a self-organizing map.

16. The system according to claim 15, wherein the physiological conditions for which the neural network has a respective output comprise at least one or more of resting, ruminating and eating and the neural network furthermore has an output for delivering a signal that is indicative of a probability that the physiological condition of the ruminant is a different one than these physiological conditions;
- wherein the system comprises a system part to be worn by the ruminant;
- wherein the system part to be worn by the ruminant is included in a housing to be worn by the ruminant around the neck;
- wherein the system further comprises a transmitting unit and a receiving unit, wherein the inertia sensor or the gyroscope, the neural network and the transmitting unit are part of a first system part to be worn by the ruminant, and wherein the receiving unit is separately included in a second system part, wherein the transmitting unit brings about that the condition data ($NT_i$) calculated by the neural network are transferred to the receiving unit of the second system part, possibly in combination with an identification code;
- wherein the first system part furthermore comprises a storage unit for storing a plurality of condition data and the transmitting unit brings about that the plurality of condition data are jointly transferred as a cluster of data to the receiving module of the second system part.

* * * * *